(12) United States Patent
Chambers

(10) Patent No.: US 6,957,697 B2
(45) Date of Patent: Oct. 25, 2005

(54) PERSONAL COOLING OR WARMING SYSTEM USING CLOSED LOOP FLUID FLOW

(76) Inventor: Paul A. Chambers, 46 Pequot Rd., Wayland, MA (US) 01778

( * ) Notice: Subject to any disclaimer, the term of this patent is extended or adjusted under 35 U.S.C. 154(b) by 101 days.

(21) Appl. No.: 10/179,165

(22) Filed: Jun. 25, 2002

(65) Prior Publication Data

US 2003/0019476 A1 Jan. 30, 2003

Related U.S. Application Data (60) Provisional application No. 60/300,635, filed on Jun. 25, 2001, provisional application No. 60/300,694, filed on Jun. 25, 2001, and provisional application No. 60/300,634, filed on Jun. 25, 2001.

(51) Int. Cl.[7] .............................................. G05D 23/00
(52) U.S. Cl. ....................... 165/297; 62/259.3; 165/46
(58) Field of Search ............................... 62/259.3, 201, 62/185; 165/297, 46

(56) References Cited

U.S. PATENT DOCUMENTS

| | | |
|---|---|---|
| 3,174,300 A | 3/1965 | Webb |
| 3,452,812 A | 7/1969 | Betts |
| 3,889,684 A | 6/1975 | Lebold |
| 4,118,946 A | 10/1978 | Tubin |
| 4,335,726 A | 6/1982 | Kolstedt |
| 4,418,745 A | 12/1983 | Roehr |
| 4,512,161 A * | 4/1985 | Logan et al. ............... 62/176.6 |
| 4,856,294 A | 8/1989 | Scaringe et al. |
| 5,320,164 A | 6/1994 | Szczesuil et al. |
| 5,603,375 A | 2/1997 | Salt |
| 5,862,675 A * | 1/1999 | Scaringe et al. ........... 62/193.3 |
| 5,871,526 A * | 2/1999 | Gibbs et al. |
| 5,878,807 A | 3/1999 | Takahashi |
| 5,970,519 A | 10/1999 | Weber |
| 6,109,338 A | 8/2000 | Butzer |
| 6,134,714 A | 10/2000 | Uglene |
| 6,238,427 B1 | 5/2001 | Matta |
| 6,500,200 B1 | 12/2002 | Kushnir |
| 6,551,347 B1 | 4/2003 | Elkins |

\* cited by examiner

Primary Examiner—Harry B. Tanner
(74) Attorney, Agent, or Firm—Pandiscio & Pandiscio (57) ABSTRACT

A garment for a personal cooling or warming system, the garment comprising a carrier formed in the shape of the garment, and a bladder comprising at least two channel segments, wherein the channel segments have a substantially flat configuration so as to improve thermal efficiency.

14 Claims, 12 Drawing Sheets

PERSONAL COOLING OR WARMING SYSTEM USING CLOSED LOOP FLUID FLOW

REFERENCE TO PENDING PRIOR PATENT APPLICATIONS

This patent application claims benefit of:

(1) now abandoned prior U.S. Provisional Patent Application Ser. No. 60/300,635, filed Jun. 25, 2001 by Paul A. Chambers for PERSONAL COOLING OR WARMING SYSTEM USING CLOSED LOOP FLUID FLOW;

(2) now abandoned prior U.S. Provisional Patent Application Ser. No. 60/300,694, filed Jun. 25, 2001 by Paul A. Chambers for AUTOMATIC CONSTANT TEMPERATURE LIQUID SUPPLY FOR CLOSED LOOP PERSONAL COOLING OR WARMING GARMENTS AND SYSTEMS; and (3) now abandoned prior U.S. Provisional Patent Application Ser. No. 60/300,634, filed Jun. 25, 2001 by Paul A. Chambers for PERSONAL COOLING OR WARMING SYSTEM USING OPEN LOOP AIR FLOW.

The three above-identified patent applications are hereby incorporated herein by reference.

FIELD OF THE INVENTION

This invention relates to cooling and warming systems in general, and more particularly to personal cooling and warming systems adapted to be worn by the user.

BACKGROUND OF THE INVENTION

In many circumstances an individual may require cooling or warming relative to an ambient environment in order to remain comfortable and, in the case of some extreme environments, in order to maintain performance and health.

In some situations the individual may be located inside a structure or the like; in this case, it is generally most efficient to cool or warm the interior of the structure, e.g., with air conditioning or heaters. This approach is generally convenient in that it allows more than one individual to be cooled or heated at the same time, and it allows the individual to remain in relative comfort regardless of their precise location within the structure.

In other situations the individual may be located in an exterior environment; in this case, it is generally not practical to cool or warm the ambient environment around the individual, particularly if the individual is moving about to a significant degree. However, where it is very hot (e.g., the southwestern border of the continental United States during the summer) or very cold (e.g., the northern border of the continental United States during the winter), and where the individual must be outdoors for prolonged periods of time (e.g., Immigration and Naturalization Service officers, other law enforcement officers, military personnel, sportsmen, etc.), it can be imperative that the individual be provided with a system to provide them with effective cooling or heating while they are outdoors.

It can also be important to provide a personal cooling or warming system for an individual when that individual must be enclosed within an impermeable protective suit, e.g., a chemical weapons protective suit, a bio-weapons protective suit, a radioactivity protective suit, etc.

SUMMARY OF THE INVENTION

As a result, a primary object of the present invention is to provide a personal cooling or warming system which may be worn by the user.

And another object of the present invention is to provide a personal cooling or warming system which is relatively simple and inexpensive to manufacture, relatively lightweight and comfortable for the user, and thermally efficient.

Still another object of the present invention is to provide a personal cooling or warming system which will remain substantially effective regardless of whether the user is standing, sitting or lying down, and regardless of whether the user is wearing heavy packs or harnesses, etc.

Yet another object of the present invention is to provide a personal cooling or warming system which may be worn beneath an impermeable protective suit.

These and other objects of the present invention are addressed by the provision and use of a novel garment for a personal cooling or warming system, the garment comprising: a carrier formed in the shape of the garment; and a bladder comprising at least two channel segments, wherein the channel segments have a substantially flat configuration.

In another form of the invention, there is provided a garment for a personal cooling or warming system, the garment comprising a bladder comprising at least two channel segments, wherein the channel segments have a substantially flat configuration.

And in another form of the invention, there is provided a novel personal cooling or warming system, the system comprising: a garment comprising a carrier formed in the shape of the garment; and a bladder comprising at least two channel segments, wherein the channel segments have a substantially flat configuration; and a fluid supply and conditioning unit for supplying temperature-conditioned fluid to the channels.

And in another form of the invention, there is provided a fluid supply and conditioning system for use in conjunction with a garment having a fluid-impervious bladder with a first port and a second port, the system comprising: a cooling/heating source having a first port and a second port; a thermostatic mixing valve having a first port, a second port and a third port; a first line; and a pump; the first line being connected to (i) the first port of the garment and (ii) the first port of the cooling/heating source and the second port of the thermostatic mixing valve; the second port of the cooling/heating source being connected to the third port of the thermostatic mixing valve; the first port of the thermostatic mixing valve being connected to the second port of the garment; and the pump being interposed into one of the first line and the fourth line; whereby when a working fluid is circulated through the garment and the fluid supply and conditioning system, the thermostatic mixing valve will ensure that fluid entering the bladder will maintain the user's body temperature at a substantially constant point.

And in another form of the invention, there is provided a personal cooling or warming system, the system comprising: a garment comprising a carrier formed in the shape of the garment; and a bladder comprising at least two channel segments, wherein the channel segments have a substantially flat configuration, and wherein the bladder further comprises a first port and a second port; and a fluid supply and conditioning system for supplying temperature-conditioned fluid to the bladder, the fluid supply and conditioning system comprising: a cooling/heating source having a first port and a second port; a thermostatic mixing valve having a first port, a second port and a third port; a first line, and a pump; the first line being connected to (i) the first port of the garment and (ii) the first port of the cooling/heating source and the second port of the thermostatic mixing valve; the second port of the cooling/heating source being connected to the third port of the thermostatic mixing valve; the first port of the thermostatic mixing valve being connected to the second port of the garment; and the pump being interposed into one of the first line and the fourth line; whereby when a working fluid is circulated through the garment and the fluid supply and conditioning system, the thermostatic mixing valve will ensure that fluid entering the bladder will maintain the user's body temperature at a substantially constant point.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Improved Garment And Bladder Constructions

The personal cooling or warming system comprises a garment which is worn by an individual so as to provide personal cooling or warming to that individual in order to enhance their comfort and performance and, in extreme cases, protect their health. This garment may take the form of a complete suit, or it may comprise a vest, shirt, pants, shorts, hat, socks, gloves, helmet liner, scarf and/or any other article of clothing. In other words, while the system can be worn as a single, complete "ensemble" garment, it may also be employed as a discrete garment component, e.g., as a vest alone, or as pants alone, or as a shirt alone, etc., so as to provide the desired level and concentration of cooling or warming. The garment is preferably worn beneath the normal clothes (e.g., beneath a uniform) of the user, and is preferably worn directly adjacent to the skin, although it may also be worn without an outer layer of clothing, and/or it may be worn over an inner layer of clothing, etc.

The garment acts as either a heat sink to rid the body of excess heat buildup (i.e., for cooling) or as a heat source to prevent excess cooling of the body (i.e., for warming), whereby to provide the user with a comfortable and healthy working environment. To this end, the garment includes a bladder which contains a working fluid (e.g., water, glycol mixtures, alcohol, etc.) which is preferably cooled or warmed (e.g., with an ice bath, a refrigerated supply source, a hot or cold thermal gel bath, an electrically heated supply, a thermo-electric heat pump, etc.) as appropriate for the desired function.

Figure 1:
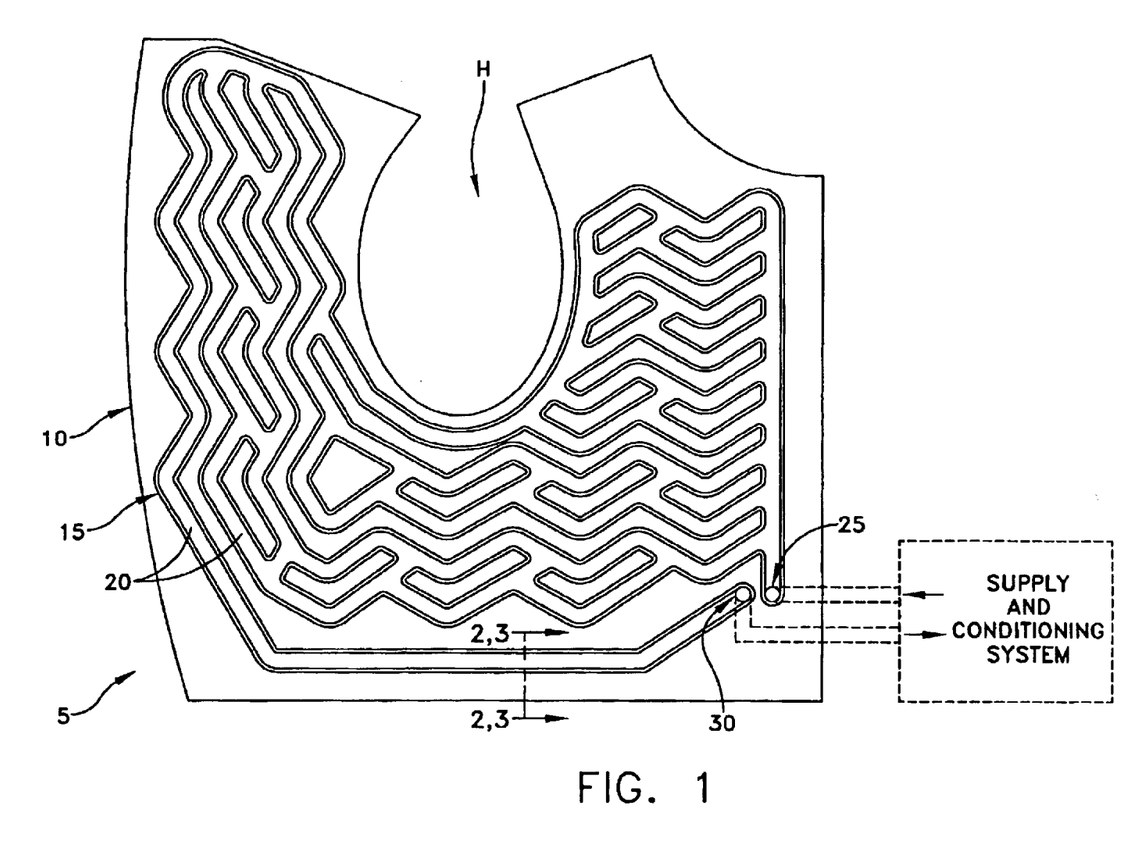
FIG. 1 is a schematic view of a personal cooling and/or warming system formed in accordance with the present invention.

More particularly, and looking now at FIG. 1, there is shown a garment 5 which is formed in accordance with the present invention. For the purposes of example but not limitation, the garment 5 shown in FIG. 1 is in the form of a vest, although other types of garments may also be formed. More particularly, the garment shown in FIG. 1 is half of a vest, i.e., the left half or the right half, with an armhole H provided in the middle of the structure.

Garment 5 generally comprises a carrier 10 to which is secured a bladder 15.

Figure 2:
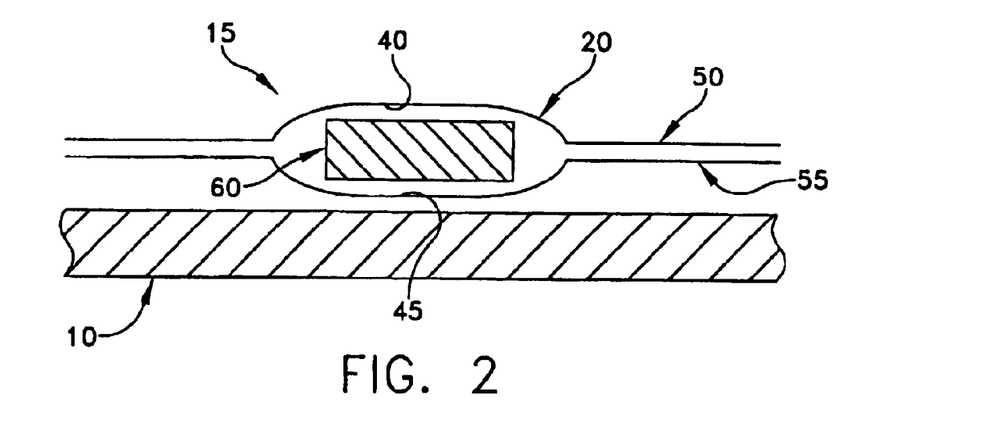
FIG. 2 is a sectional view taken along line 2—2 of FIG. 1.
Figure 12:
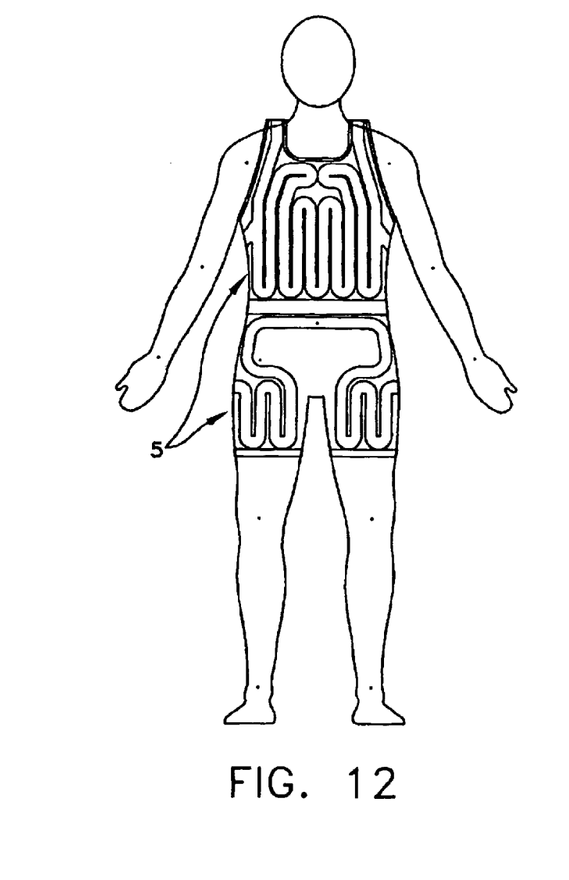
FIG. 12 is a schematic view showing several different garments formed in accordance with the present invention and being worn simultaneously by a user.
Figure 13:
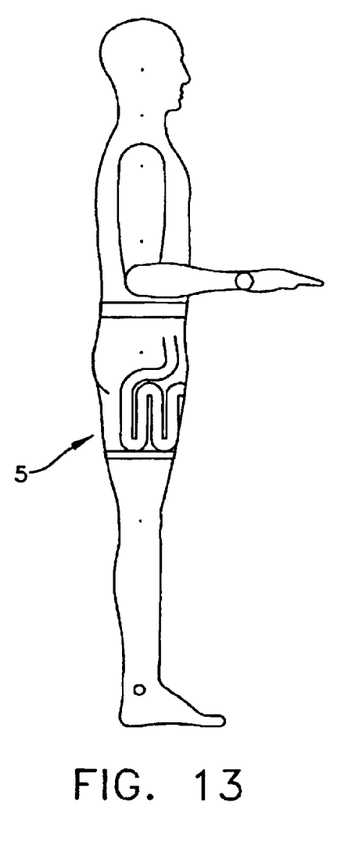
FIGS. 13 and 14 are schematic views showing how the bladder may be applied to only selected portions of the garment.
Figure 14:
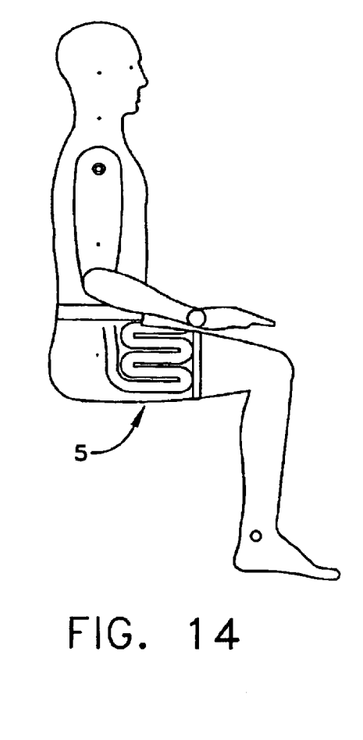

Carrier 10 preferably comprises one or more pieces of fabric or the like which is formed in the shape of the garment desired, e.g., in the shape of the vest shown in FIG. 1, or in the shape of an athletic shirt (also sometimes referred to as an "A shirt" or "tank top") such as shown in FIGS. 6–10B, or in the shape of shorts such as shown in FIGS. 12–14, etc. Carrier 10 is formed out of a material which is capable of supporting bladder 15 and which provides good thermal transmission to and from the underlying skin. If desired, carrier 10 may be formed out of a material such as cotton, or a fleece-like material such as Polartec®, or an integrated, unitary, semi-elastic knitted or woven material, etc. If necessary, carrier 10 may be fitted with various snugging-down and/or closure devices (e.g., Velcro™ snaps) so as to ensure a close fit with the body of the user. Carrier 10 may comprise a single layer of material (FIG. 2), to which bladder 15 is secured; alternatively, carrier 10 may comprise two layers of material (FIG. 3), one on each side of the bladder, with the bladder being secured to one or both layers of fabric so as to form a laminated unitary garment.

Bladder 15 is preferably in the form of a series of interconnected, convoluted channels 20 that provide multiple, redundant flow paths along at least part, and preferably substantially all, of the garment. Preferably bladder 15 includes an input port 25 (FIG. 1) and an output port 30 (FIG. 1) by which the working fluid may be introduced into, and withdrawn from, channels 20. Preferably channels 20 are arranged so as to effect a reasonably even flow throughout the garment. This even flow distribution may be achieved through the relative sizing of the channels 20 and/or through the use of flow diverters (not shown) located at the point where a given channel branches into two or more subsequent channels. This even flow distribution can be important, particularly with a complex garment such as a vest with differential loading (e.g., where a heavy load is carried on the back) and/or where several garments are worn together.

Figure 3:
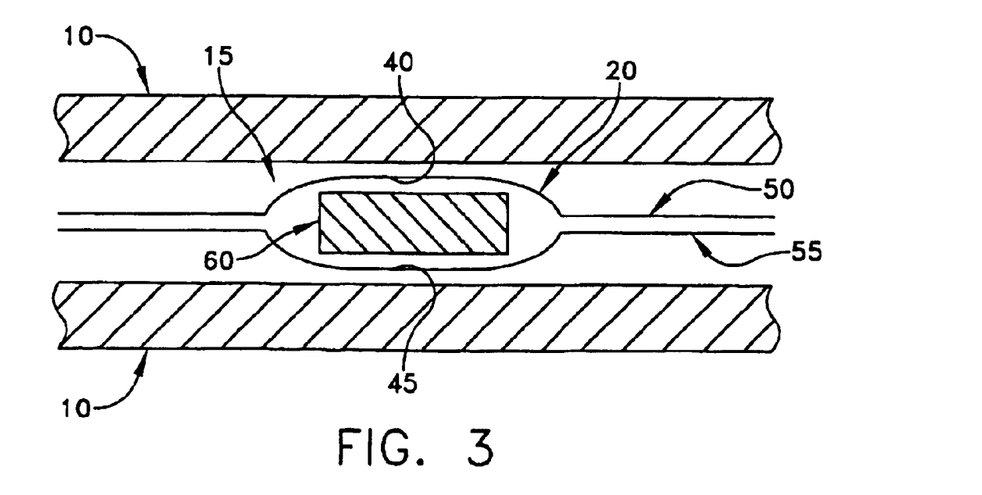
FIG. 3 is a sectional view taken along line 3—3 of FIG. 1.

Each of the flow channels 20 is preferably fabricated as a substantially flat tube (FIGS. 2 and 3) between two opposing walls 40, 45. In one preferred form of the invention, this is achieved by placing two relatively large sheets 50, 55 in opposing relation to one another and then bonding them together (e.g., with heat sealing) at selected locations so as to form the fluid-tight channels, with subsections of sheets 50, 55 forming the opposing walls 40, 45. One or both of the two relatively large sheets 50, 55 may then be mounted to carrier 10 depending on whether carrier 10 comprises a single layer of material (FIG. 2) or two layers of material (FIG. 3). If desired, where bladder 15 is fabricated out of relatively large sheets of material, some or all of the "unused" sheet material extending between channels 20 may subsequently be removed, e.g., by die cutting. Removal of such material may render bladder 15, and hence garment 5, more flexible.

The bladder's opposing walls 40, 45 are formed out of a fluid-impermeable material which is assembled so as to form the fluid containing channels 20. In one preferred form of the invention, opposing walls 40, 45 are formed out of polyurethane. More particularly, in one preferred form of the invention, bladder 15 is preferably fabricated from two large sheets 50, 55 of polyurethane sheet stock, with the specific material selection being a function of the intended working fluid, the system's required pressure, the garment's required flexibility, etc., and may be custom tailored to a particular application. By way of example but not limitation, bladder 15 may be fabricated from 0.009 or 0.015 inch thick natural, ether-based, PT 9200 polyurethane sheets of the type produced by Deerfield Urethane of South Deerfield, Mass.

A ribbon 60 is preferably disposed in channels 20, between opposing walls 40, 45. Ribbon 60 is formed out of a material which is relatively impervious to the working fluid flowing in channels 20 and relatively resistant to compressing. The ribbon 60 is preferably attached to both of the opposing walls 40, 45, whereby to help hold channels 20 in their desired flat configuration. Alternatively, however, ribbon 60 may be attached to only one of the opposing walls 40, 45 (e.g., the outer wall 40); in this case, the flat configuration of channels 20 may be maintained by appropriately fashioning opposing walls 40, 45 and securing them to carrier 10.

The flat configuration of channels 20 and the presence of ribbon 60 therein together provide several important functions:

(1) the flat cross-section of channels 20 maximizes skin contact area for more efficient heat transfer;

(2) the presence of ribbon 60 in channels 20 reduces the volume of fluid required for a given channel diameter and contact area, thereby reducing the overall fluid volume (and weight) of the system—in other words, inasmuch as the ribbon 60 takes up considerable volume within the channel 20 (e.g., over 50% in some designs) but does not reduce the effective area of fluid in contact with the skin, it reduces the volume of fluid required to fill the garment's bladder while still providing the desired contact area;

(3) the ribbon 60 minimizes "squeeze-off" of fluid flow caused by, for example, point pressure from restraint harnesses (e.g., safety belts) or load-carrying harnesses (e.g., SCBA Packs), etc., or from area pressure imposed by the user sitting on or leaning against a firm surface—more particularly, since the ribbon 60 is relatively resistant to compressing, and hence can only be compressed so far, it always provides a degree of physical separation between the two opposing walls 40, 45 of the flat channel, and hence always ensures a flow path for fluid to pass between the sides of the ribbon and the side edges of the channel: and to optimize this performance, the ribbon 60 can have varying degrees of density and stiffness according to the location in the garment (e.g., in the case of a vest, the ribbon in the upper back region could be stiffer so as to better resist the "squeeze-off" from heavy loads); and (4) the ribbon 60 can be secured to the inside face of the wall 40 and so effect all of the foregoing functions even while minimizing the surface area of fluid which is exposed to the ambient conditions on the outside face of the channels and garment—this minimized exposure of the working fluid to the environment, plus the insulating properties of the ribbon 60, minimizes heat gain/loss to the environment from the working fluid, thereby maximizing the thermal capacity available for cooling/warming the body of the user.

The ribbon 60 may be fabricated out of any material which is consistent with one or more of foregoing functions. By way of example but not limitation, in one preferred form of the invention, ribbon 60 is formed out of a closed cell foam. And in one particularly preferred form of the invention, ribbon 60 is formed out of 2 pound, 3/16 inch thick, white vellum closed cell foam material of the type produced by New England Foam of Hartford, Conn.

Input port 25 (FIG. 1) and output port 30 (FIG. 1) may be any fittings which are consistent with delivering fluid to, and removing fluid from, bladder 15. In one preferred form of the invention, these fittings are configured as simple "female" couplers that can interface to any supply and return line system through appropriately-sized "barbed" male fittings. By way of example but not limitation, these fittings may be No. 727 Acur right angle valves of the type produced by Halkey Roberts of St. Petersburg, Fla. These female fittings connect to male quick connect couplers used to deliver fluid to, and remove fluid from, the system, e.g., such as male quick connect couplers of the type available from Colder Products Company, St. Paul, Minn. The garment 5 is constructed so that input port 25 and output port 30 are exposed for easy connection to liquid supply and return lines. These fittings may be positioned anywhere on the garment to protrude from the outer face thereof, or from an edge thereof so as to provide maximum comfort when worn under a heavier outer garment (e.g., an armored vest). In the case where input port 25 and output port 30 are on the same side of the garment as a layer of carrier 10, the layer of the carrier is recessed (e.g., either by terminating the carrier short of the fittings or by forming holes in the carrier) so as to facilitate easy access to the inport port 25 and the output port 30.

The garment 5 is designed to facilitate large-scale, semi-automated manufacturing at minimum cost. To this end, each garment is preferably fabricated from identical halves that are assembled together in a mirrored manner so as to produce the complete garment. Each component of the garment (carrier 10, bladder 15 and ribbons 60) are preferably die cut and then assembled on jigs in order to quickly and reliably locate them in the correct relative positions. The bladder sheets, inlet and outlet fittings, and foam ribbons are preferably RF welded and/or thermally welded and/or adhesively bonded into a two-ply laminate sub-assembly in a single welding operation; this sub-assembly is then secured to the carrier with a combination of adhesive and sewn edge taping. The adhesive is preferably a heat activated adhesive film of the type produced by Bemis Co. of Shirley, Mass. Alternatively, the bladder sheets, inlet and outlet fittings and foam ribbons are preferably secured to one another, and the bladder secured to the carrier, in a single welding or bonding operation. In one preferred form of the invention, the bladder is preferably secured to the carrier via a welding or other heating process so that the material of the bladder extrudes into the weave or the pores of the carrier so as to effect a secure attachment. Among other things, this construction provides greater flexibility to the garment.

Figure 4:
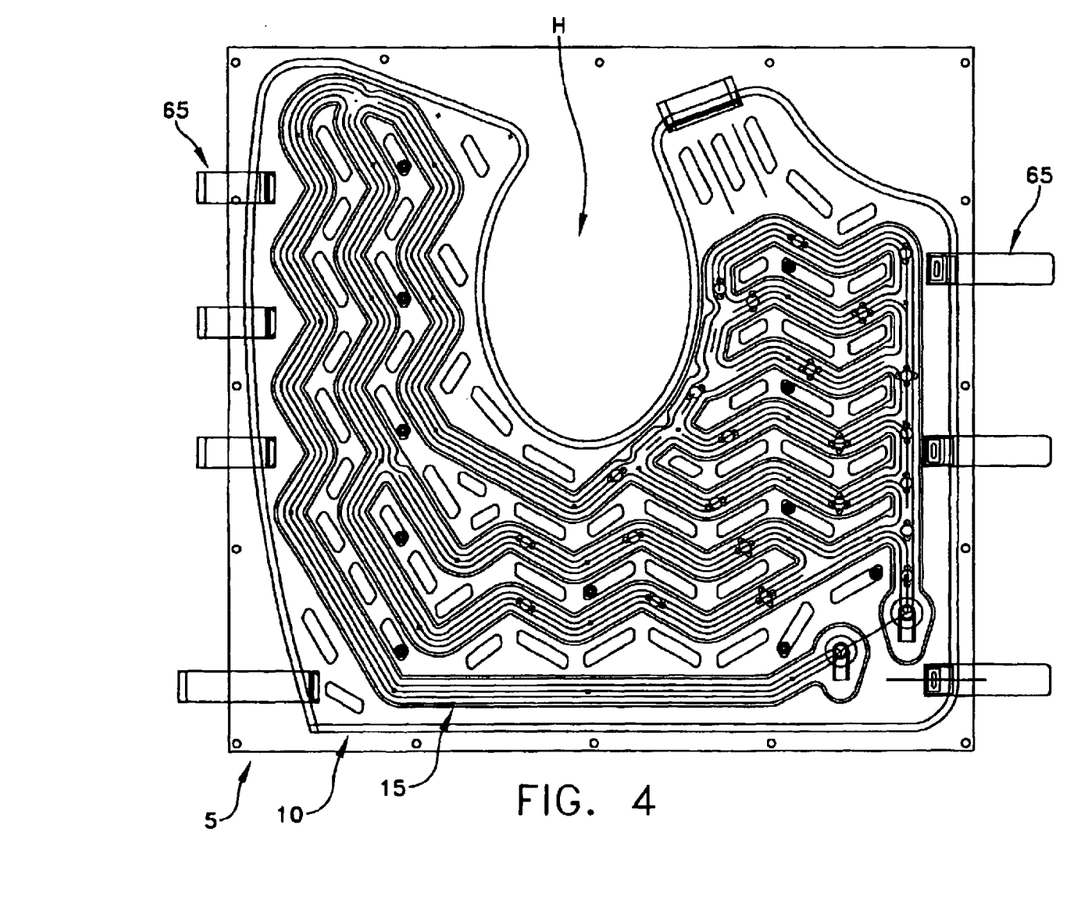
FIG. 4 is a schematic view showing one half of a vest garment.
Figure 5:
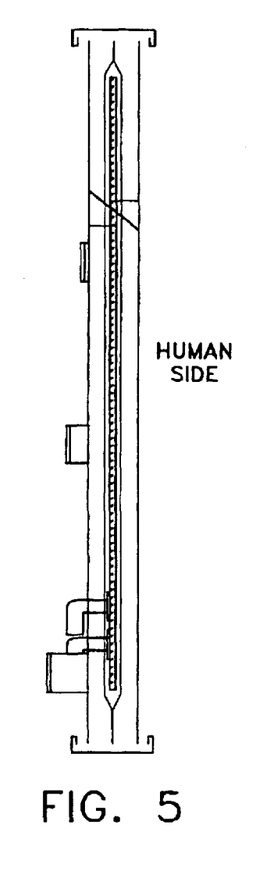
FIG. 5 is a sectional view taken along line 5—5 of FIG. 4.

By way of example but not limitation, the embodiment shown in FIGS. 4 and 5 is half of a vest, i.e., the left half or the right half, with the armhole H formed therein. The closure system preferably comprises Velcro® hook and loop fastener tape 65 sewn to both sides of the front of the vest. Elastic panels are then sewn onto the garment as the connection between the two halves of the vest down the spine joint line. This elastic provides some stretch to the vest and allows it to snug onto the user and to accommodate different user sizes and shapes and to maintain optimum skin contact.

Figure 6:
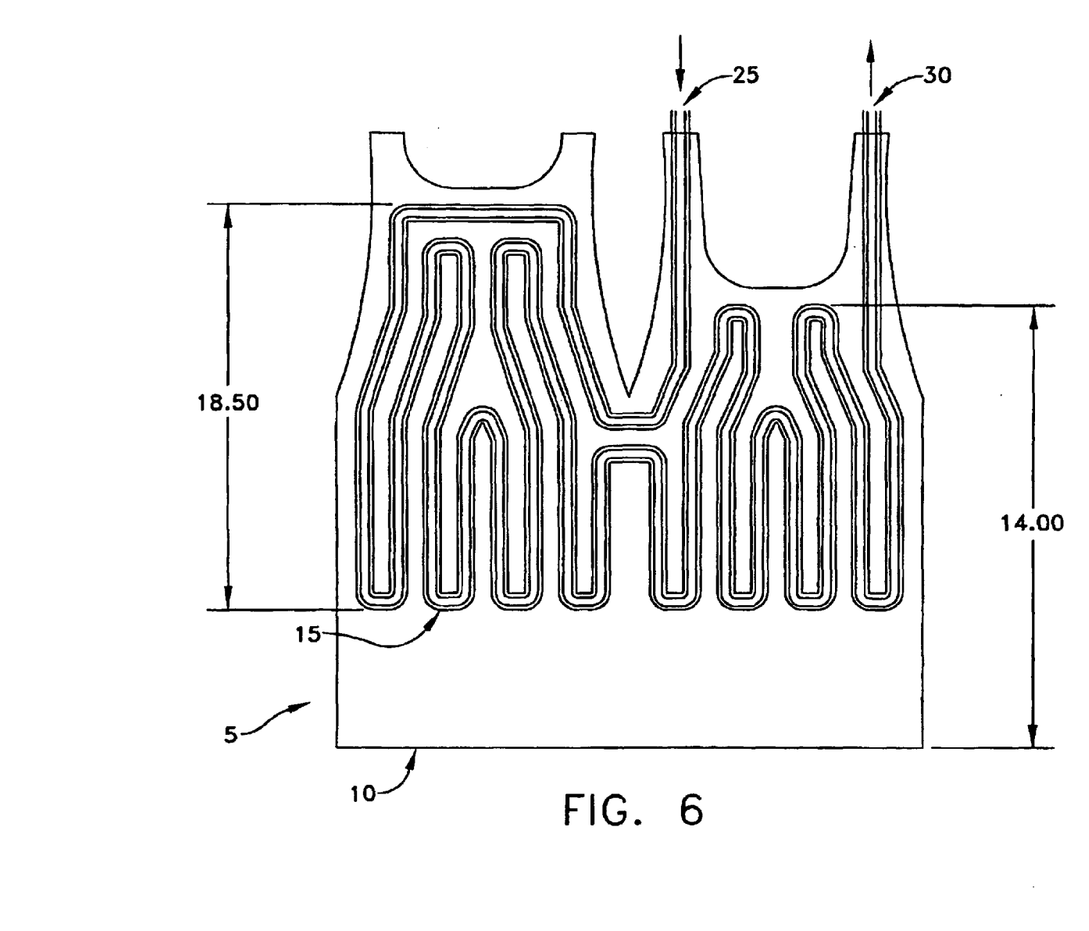
FIG. 6 is a schematic view showing another form of garment formed in accordance with the present invention.

By way of further example but not limitation, the embodiment shown in FIG. 6 is an athletic shirt formed out of single assembly, with the front and back sides of the shirt initially in side-by-side relation. At a subsequent stage of manufacture, the front and back sides are folded against one another and then secured together so as to form the complete shirt. In this situation, and particularly where the carrier material has some elasticity to it, the system may not require additional closure systems.

Figure 7:
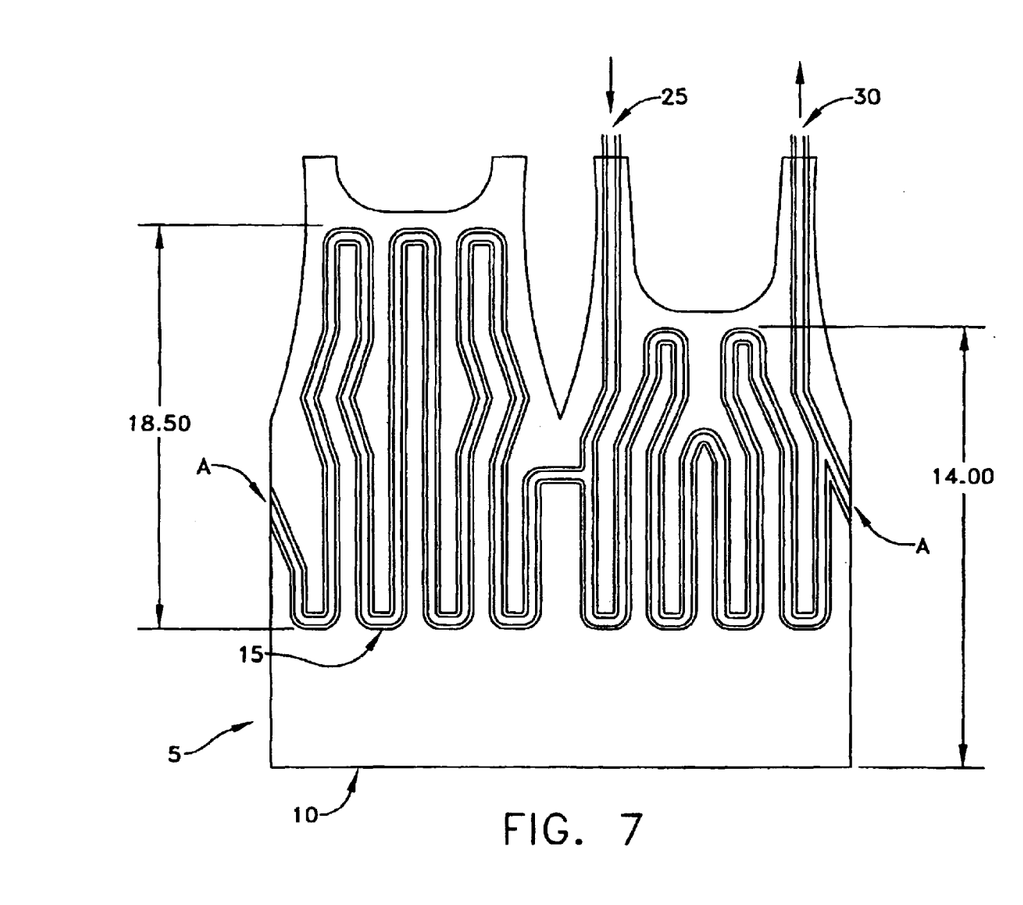
FIG. 7 is a schematic view showing still another form of garment formed in accordance with the present invention.

FIG. 7 shows an athletic shirt which is generally similar to the shirt shown in FIG. 6, except that with the shirt of FIG. 7, fresh fluid entering input port 25 is directed to the two halves of the shirt in parallel, rather than serially as is the case with the shirt of FIG. 6. With the construction of FIG. 7, channel ends A are connected together when the two halves of the shirt are joined so as to enable proper fluid flow.

Figure 8:
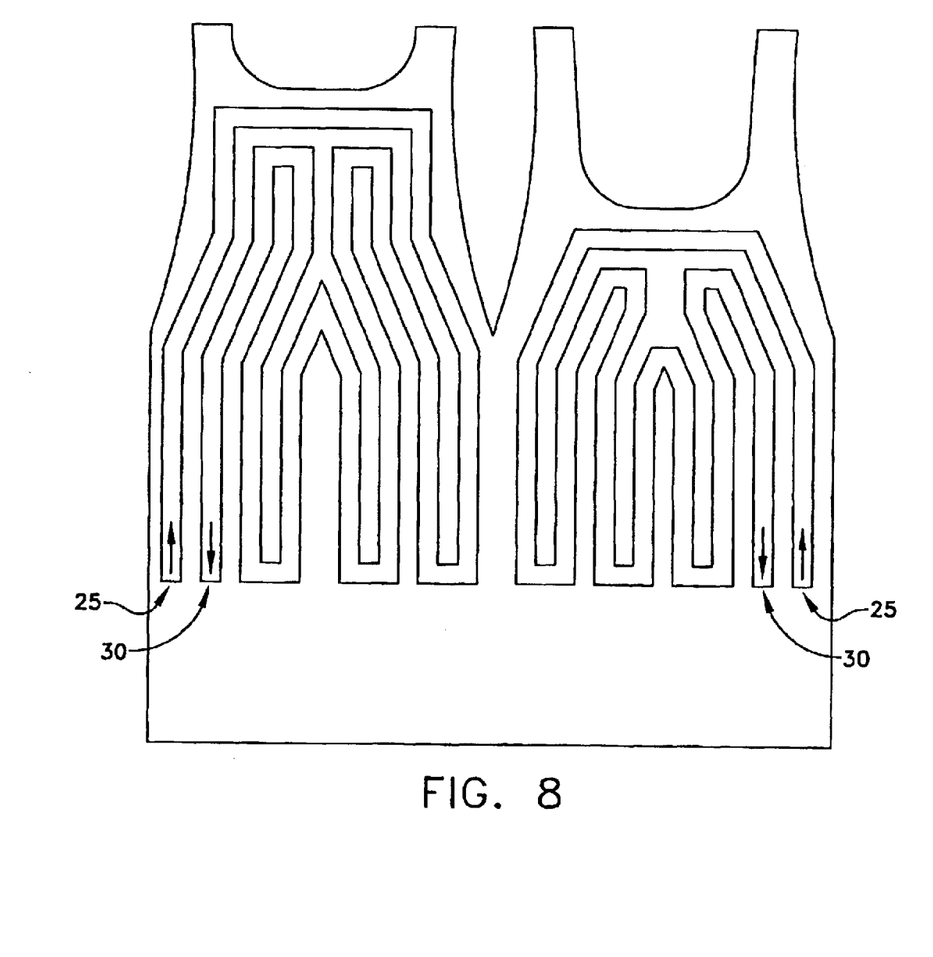
FIG. 8 is a schematic view showing yet another form of garment formed in accordance with the present invention.

FIG. 8 shows another possible athletic shirt construction for applying fresh fluid to both halves of the shirt in parallel: here, each half of the shirt has its own independent network of channels 20, and each half of the shirt has its own input port 25 and output port 30.

Figure 9A:
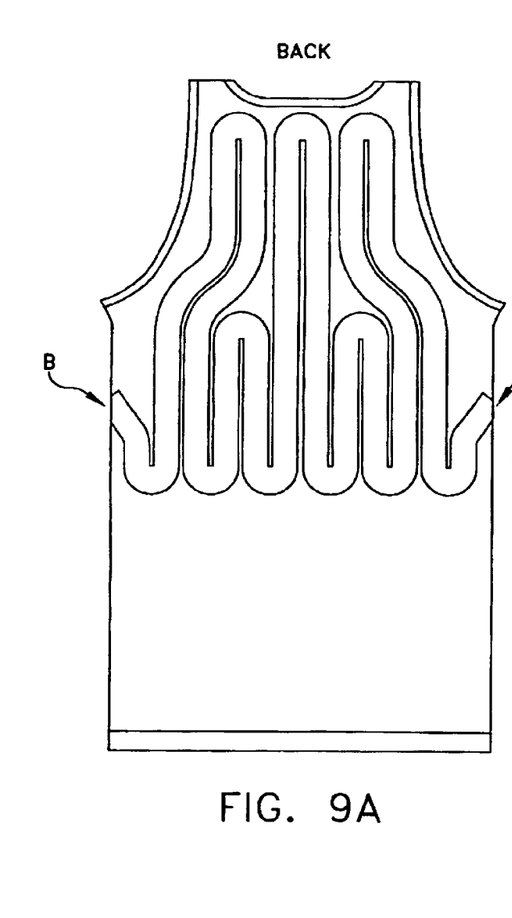
FIGS. 9A and 9B are schematic views showing another form of a garment formed in accordance with the present invention.
Figure 9B:
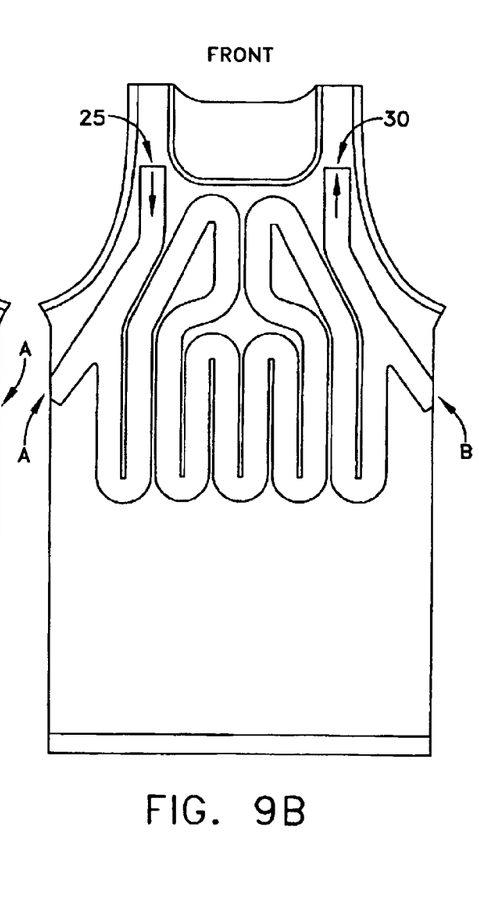
Figure 10A:
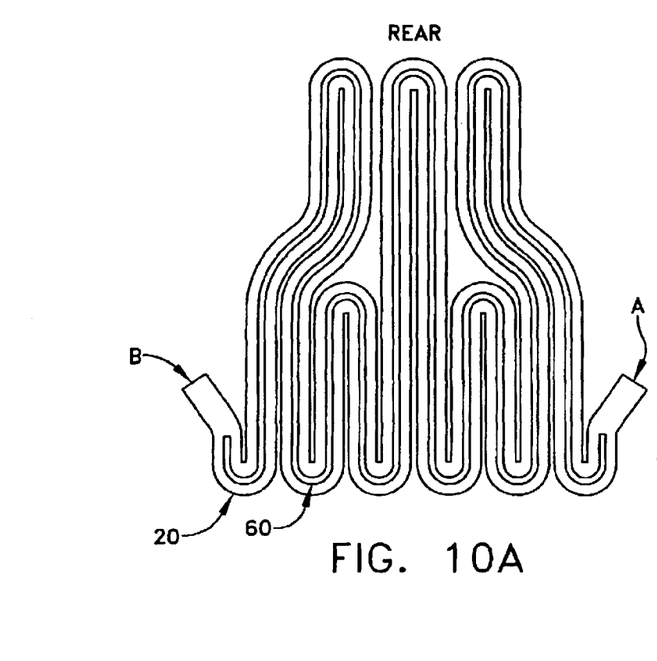
FIGS. 10A and 10B are schematic views showing the bladder construction for the garment shown in FIGS. 9A and 9B.
Figure 10B:
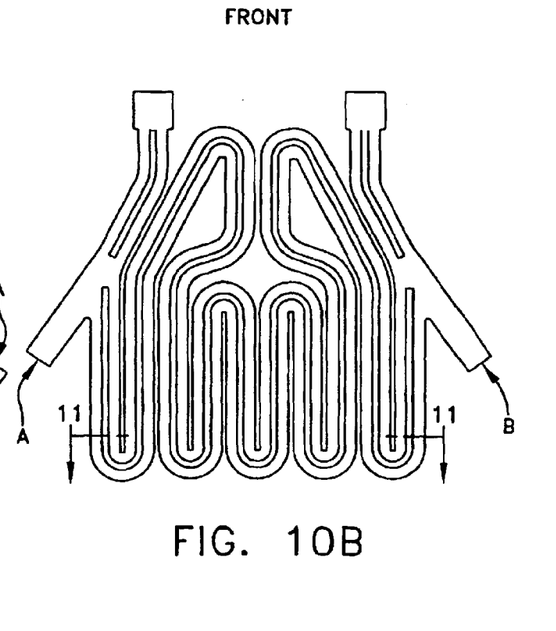
Figure 11:
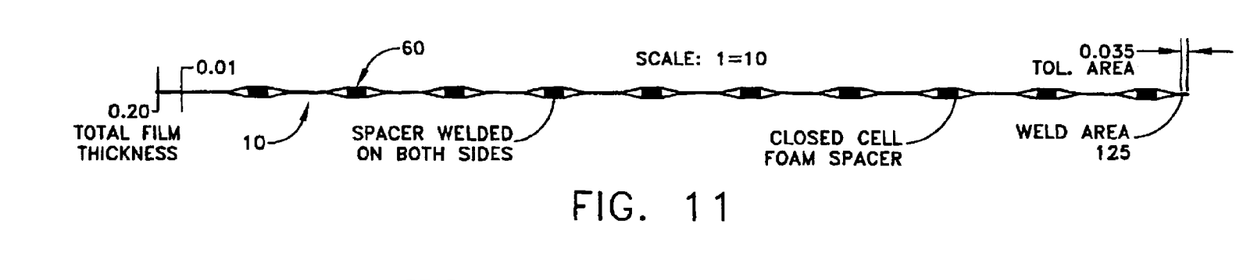
FIG. 11 is a sectional view taken along line 11—11 of FIG. 10B.

FIGS. 9–11 show still another possible athletic shirt construction. Here, the garment comprises two halves, each with its own unique channel pattern. One of the halves has input port 25 and output port 30. When the two halves of the shirt are joined together so as to form the complete garment, channel ends A are connected together and channel ends B are connected together, whereby to enable proper fluid flow.

FIG. 12 illustrates how separate garments 5 (e.g., an athletic shirt and shorts) may be combined for the desired anatomical coverage. In this respect it should be noted that each of the garments may receive fluid directly from the fluid source (i.e., in parallel to one another); or the garments may be linked together so that the output of one is fed to the input of another (i.e., so that the garments are linked in series with one another). It should also be appreciated that the garments may be linked to one another so that one of the garments receives fluid from the fluid source and that garment is adapted to supply fluid to, and receive fluid from, a second garment such that the flow through that second garment is in parallel to the flow through the first garment.

FIGS. 13 and 14 illustrate how channels 20 may be disposed over only selected portions of the garment if desired.

Garment 5 is intended to be used as follows.

Temperature controlled fluid (either cooled or warmed relative to the user's body surface temperature) is pumped to the garment from the supporting fluid supply and conditioning system via the inlet fitting(s). This supporting fluid supply and conditioning system may be any one of the fluid supply and conditioning systems known in the art and consistent with the present invention. The line pressure of the fluid (e.g., 10 gallons per hour at 3–4 psi) is sufficient to distend the flow channels, thereby providing regions around the enclosed ribbon 60 through which the fluid flows. This flowing fluid acts as a heat exchanger with the body of the user through several heat transfer mechanisms, including:

(1) direct conduction from the skin into the fluid through the bladder wall (and through any intervening carrier layer which may be present);

(2) convection from the air layer surrounding the body and captured by the user's clothing; and (3) evaporative cooling by the wicking action of the sweat through the fabric liner (if the garment includes a carrier layer interposed between the body of the user and the bladder).

The fluid is channeled around and through the garment in a controlled manner which is achieved through the bladder channel design (e.g., the relative sizing of the channels 20) and/or the incorporation of flow diverters (not shown) at channel branch points. The flow exits the garment through the outlet fitting(s). The working fluid returns from this point to the conditioning unit to be re-cooled or re-heated as appropriate.

System performance is generally a function of flow rate (typically in the range of 5–12 gallons per hour), the thermodynamic capacity of the working fluid, the working fluid-to-body skin temperature differential, the effective heat exchange contact area, the thermal transmission co-efficients of system materials, etc. In this respect it will be appreciated that only the last two items are characteristics of the garment system; the remainder of the items are functions of the fluid supply and conditioning system.

The fluid supply and conditioning system may be any system which can provide sufficient flow and pressure (e.g., 5–10 gallons per hour, at 3–4 psi) of the cooled or warmed fluid (as appropriate) to the garment. This could be a refrigerated reservoir (e.g., chilled by ice, a previously frozen thermal gel or thermo-electric modules) or heated supply (e.g., warmed by a previously heated thermal gel or thermo-electric modules). The conditioned fluid is then driven around the circuit by a small electric pump. The system is preferably fitted with control valves and flow limiters as necessary so as to provide control to the wearer. By way of example but not limitation, liquid conditioning may be accomplished with ice packs, MicroCore® and Cool Ice® thermal gel packs, and a Ferrotec™ or MELCOR™ thermo-electric module-based heat exchanger. The circulating pump used may be of the type available from Smart Pumps, Inc., San Jose, Calif.; Hargraves Technology Corp., Mooresville, N.C.; and PAR Technologies, Newport News, Va.

If desired, and depending on the nature of the cooling/warming system supplying the garment, a thermostatic switch (thermostat) may be integrated into or onto the garment to monitor fluid temperature and to supply input to the control system for the fluid supply and conditioning unit.

Various advantages are achieved through the use of the present invention. Among these are:

(1) fluid flow is substantially prevented from being squeezed off by normal body/seat, body/harness, etc., contact pressure;

(2) flow channels are designed to maintain their flat shape and, aided by the enclosed ribbons 60, maximize heat exchange contact area and hence efficiency;

(3) flow channels partially filled by the ribbons 60 minimize fluid volume requirements, thereby minimizing system weight and fluid reservoir volume;

(4) universal inlet and outlet fittings allow maximum interchangeability with existing fluid supply and conditioning systems and provide ease of interface to all fluid supply and conditioning systems;

(5) elastic panels and adjustable closures or, more preferably, the use of somewhat elastic, skin-friendly (e.g., natural cotton) carrier materials maximize the quality of the garment fit and hence system heat exchange efficiency;

(6) the system's laminated configuration allows for simple semi-automated assembly at minimum cost; and (7) the streamlined cross-section of the garment and its welded fabrication maximizes durability and resistance to wear during the normal laundering process, thereby maximizing garment life.

It should also be appreciated that various modifications may be made to the embodiments described above without departing from the scope of the present invention.

Thus, for example, in the preceding discussion it was indicated that opposing walls 40, 45 of channels 20 are preferably formed by selectively bonding together two relatively large sheets 50, 55 of material. However, if desired, opposing walls 40, 45 may be formed by long strips of material which are bonded together along their parallel outer edges, with one of the walls 40, 45 then being mounted to carrier 10.

It is also contemplated that bladder 15 may be formed by two large sheets 50, 55 of material selectively bonded together so as to form the channels 20; by forming bladder 15 with the proper shape (e.g., in the shape of a vest), it may then be worn as is, without the addition of the carrier 10.

Still other changes will be obvious to persons skilled in the art in view of the present disclosure.

Improved Fluid Supply And Conditioning System

With conventional fluid supply and conditioning systems, the working fluid is cooled or warmed at a site remote from the garment, passed to the input port of the garment, circulated through the garment's bladder so as to effect the desired heat-exchange function, passed out the output port of the garment and then returned to the aforementioned remote site, where the working fluid is re-cooled or re-heated before being re-circulated back to the garment.

Conventional fluid supply and conditioning systems have no temperature control per se. More particularly, conventional fluid supply and conditioning systems generally have a source of cooling or warming (e.g., an ice bath, a refrigerated supply source, a hot or cold thermal gel bath, an electrically-heated supply, a thermo-electric heat pump, etc.). Unfortunately, these systems tend to supply uncomfortably cold or hot fluids to the garment initially, when the system's cooling/heating source is fully charged; this can result in significant user discomfort and inefficient use of the system's cooling/heating source. Thereafter, when the system's cooling/heating source has been partially or fully depleted, they tend to supply heated-up or cooled-down fluids to the garment, thus providing reduced system performance. This problem can be particularly significant where the source of cooling or warming consists of a "single use" mechanism, e.g., an ice bath, hot or cold thermal gel baths, etc.

In an attempt to overcome these problems, some systems provide the user with some degree of flow control (e.g., flow control valves, adjustable pumps, etc.) so that the user may adjust fluid flow and hence, to some extent, system performance. However, these measures still fail to supply the working fluid to the garment at a relatively constant temperature for the life of the cooling/heating source.

Figure 15:
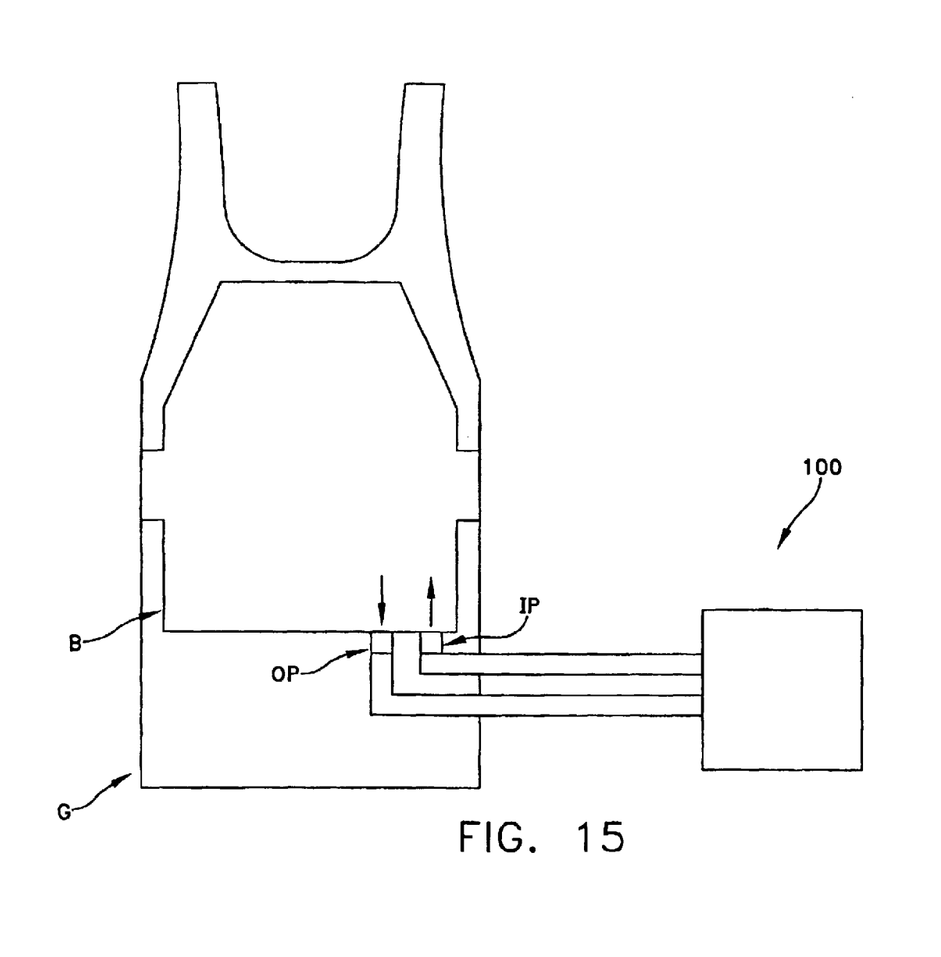
FIG. 15 is a schematic view illustrating a novel fluid supply and conditioning system formed in accordance with the present invention.

Looking next at FIG. 15, there is shown a novel fluid supply and conditioning system 100 formed in accordance with the present invention. System 100 may be used in conjunction with any cooling or warming garment G which includes a fluid-impervious bladder B having input port IP and output port OP. By way of example, system 100 may be used with the garment 5 described above, including its bladder 15, input port 25 and output port 30; alternatively, system 100 may also be used with other cooling or warming garments consistent with the present invention.

Figure 16:
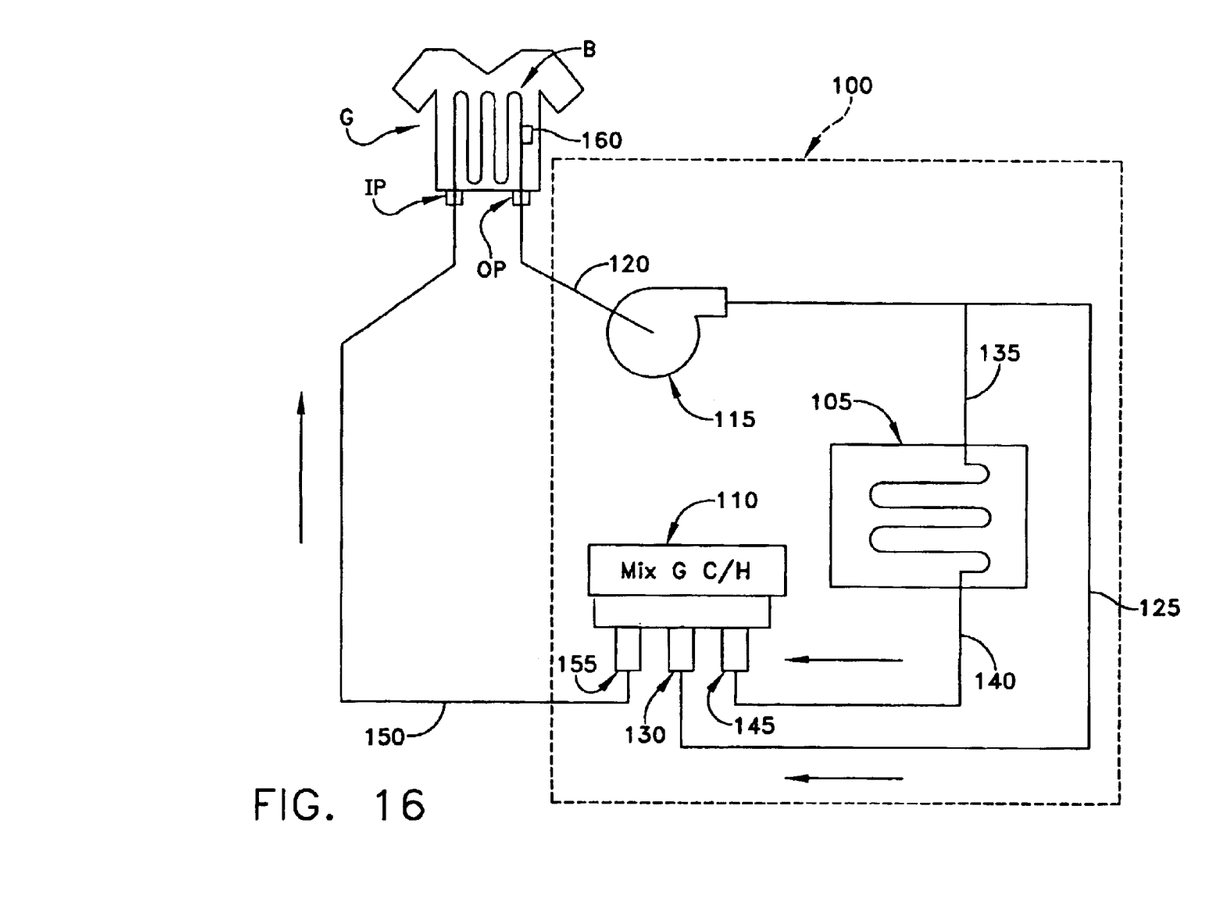
FIG. 16 is a schematic view illustrating construction details of one embodiment of the fluid supply and conditioning system shown in FIG. 15.

Looking next at FIG. 16, fluid supply and conditioning system 100 is shown in greater detail. Fluid supply and conditioning system 100 generally comprises a cooling/heating source 105, a thermostatic mixing valve 110 and a pump 115. A first line 120 connects the output port OP of garment G with the input of pump 115; a second line 125 connects the output of pump 115 with an input 130 of thermostatic mixing valve 110; a third line 135 connects the output of pump 115 with the input of cooling/heating source 105; a fourth line 140 connects the output of cooling/heating source 105 with an input 145 of thermostatic mixing valve 110; and a fifth line 150 connects the output 155 of thermostatic mixing valve 110 with the input port IP of garment G.

Cooling/heating source 105, thermostatic mixing valve 110, pump 115 and lines 120, 125, 135, 140 and 150 together form a closed system so that the working fluid may be driven around the system under a pressure appropriate for the garment G. Lines 120 and 150 are preferably formed with "universal interface" connectors so that fluid supply and conditioning system 100 may be quickly and easily used with any garment G consistent with the present invention.

Cooling/heating source 105 is preferably a closed reservoir containing the means by which the working fluid is cooled or heated. By way of example, cooling/heating source 105 may comprise a closed, insulated container housing the source of cooling or warming (e.g., an ice bath, a refrigerated supply source, a hot or cold thermal gel bath, an electrically-heated supply, a thermo-electric heat pump, etc.). In one preferred form of the invention, fluid conditioning is achieved using ice packs for cooling. In another preferred form of the invention, fluid conditioning is achieved using MicroCore® and Cool Ice® thermal gel packs. In still another preferred form of the invention, fluid conditioning is achieved using Ferrotec™ or MELCOR™ thermo-electric module-based heat exchangers.

Thermostatic mixing valve 110 comprises a small thermostatic mixing valve/diverter. More particularly, thermostatic mixing valve 110 is of the type known in the fluid-handling art, comprising three ports: one for a higher temperature fluid, one for a lower temperature fluid, and one for a mixture of the two. The valve is pre-configured for a given mixture temperature, and includes internal components that automatically adjust the flow ratios of the higher and lower temperature lines in accordance with the same. In the present invention, thermostatic mixing valve 110 is used to control how much of the working fluid is sent to cooling/ heating source 105 for temperature conditioning and how much of the working fluid is sent directly back to the garment without temperature conditioning. By varying this ratio appropriately, the fluid in garment G may be maintained at a substantially constant temperature. This approach maximizes system efficiency and user comfort. In this respect it should also be appreciated that the same type of thermostatic mixing valve 110 may be used for both cooling and heating applications. Of course, since the thermostatic mixing valve 110 is pre-set to a particular target mixture temperature, different valves must be used for cooling and heating. More particularly, where the system is to be used for cooling, it is generally preferred that the thermostatic mixing valve be pre-set to a temperature slightly below room temperature (e.g., 65° F.); and where the system is to be used for heating, it is generally is preferred that the thermostatic mixing valve be pre-set to a temperature slightly above body temperature (e.g., 105° F.). One preferred thermostatic mixing valve is a thermostatic mixing valve (Part No. 1/8 ID-B M/D 70F) produced by Therm-Omega-Tech, Inc., of Warminster, Pa.

Pump 115 is preferably a high efficiency, low voltage electric pump adapted to drive the working fluid around the system. This pump may be any pump consistent with the present invention, however, it is preferably a 12 volt dc pump for vehicle-mounted systems and it is preferably a 6 volt dc pump for man-pack versions. By way of example but not limitation, pump 115 may be a diaphragm pump of the type produced by Smart Pumps, Inc., San Jose, Calif. (12 volt dc version) or Hargraves Technology Corp., Mooresville, N.C. (6 volt dc version). By way of further example but not limitation, pump 115 may be a small, low power draw 3–9 volt dc piezo-electric pump such as the PHD Piezuator pump available from PAR Technologies, Inc., Newport News, Va. Pump 115 may also be a gear pump of the sort known in the fluid-handling art. In one form of the invention, pump 115 is activated by the user through the use of an ordinary on-off switch (not shown).

The fluid supply and conditioning system 100 shown in FIG. 16 essentially operates as follows. After initial priming, thermostatic mixing valve 110 sets the mix ratios of its input port 130 and its input port 145 so as to achieve the desired (i.e., pre-set) fluid temperature at the mixing valve's output port 155. On the basis of this mix ratio, pump 115 will cause corresponding proportions of working fluid to move (i) through second line 125 and into input port 130 ("garment output fluid"), and (ii) through third line 135, cooling/heating source 105, fourth line 140 and into input port 145 ("cooling/heating source output fluid"). As a result, the proper blend of garment output fluid and cooling/heating source output fluid will be effected so as to achieve the desired fluid temperature at the valve's output port 155. Thus it will be seen that, as a result of this construction, the working fluid supplied to the garment's input port IP will remain at a substantially constant temperature over the life of the cooling/heating source 105. This represents a significant improvement over existing systems.

Figure 17:
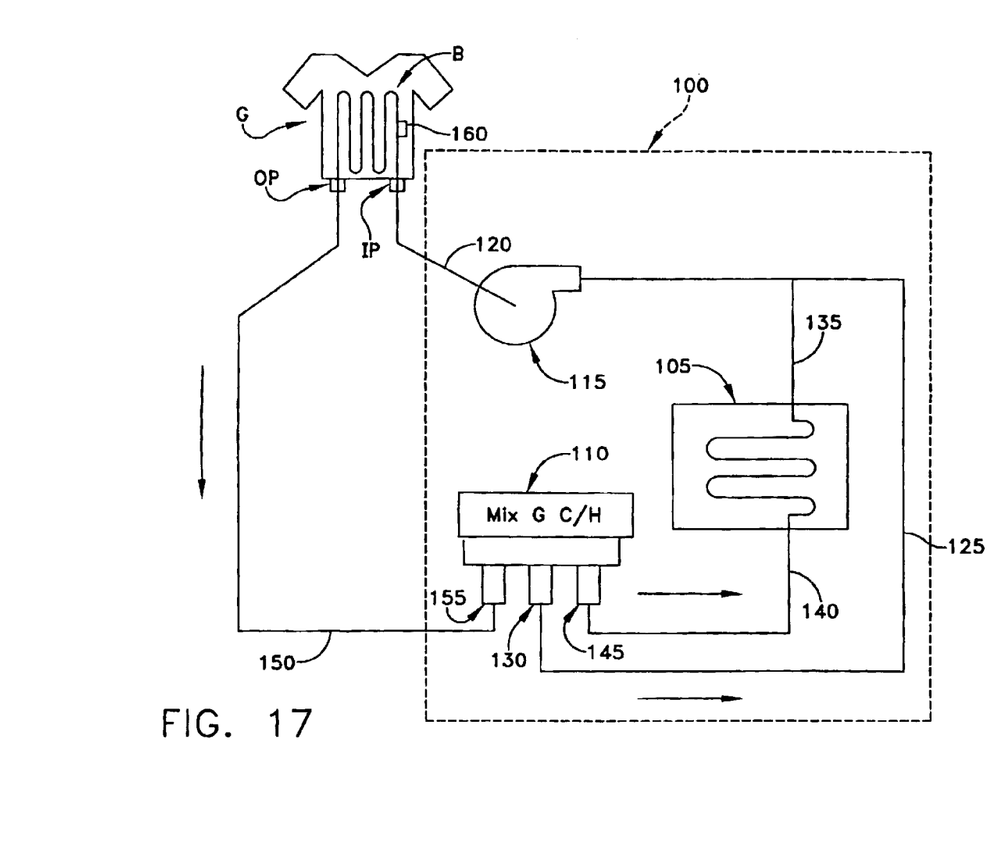
FIG. 17 is a schematic view illustrating construction details of another embodiment of the fluid supply and conditioning system shown in FIG. 15.

Looking next at FIG. 17, there is shown an alternative form of the invention. Here, the flow of the system is reversed, i.e., it is used to draw fluid through thermostatic mixing valve 110 before a portion of that fluid is passed through cooling/heating source 105. In this arrangement, first line 120 connects the input port IP of garment G with the output of pump 115; second line 125 connects the input of pump 115 with the output port 130 of thermostatic mixing valve 110; third line 135 connects the input of pump 115 with the output of cooling/heating source 105; fourth line 140 connects the input of cooling/heating source 105 with output port 145 of thermostatic mixing valve 110; and fifth line 150 connects the output port OP of garment G with the input port 155 of thermostatic mixing valve 110.

The fluid supply and conditioning system 100 shown in FIG. 17 essentially operates as follows. After initial priming, thermostatic mixing valve 110 sets the relative ratios of its output port 130 and its output port 145 according to the temperature of the fluid entering the mixing valve's input port 155 and the mixing valve's pre-set (i.e., target) temperature. On the basis of this mix ratio, corresponding proportions of working fluid are moved (i) through output port 130 and second line 125 ("garment output fluid"), and (ii) through output port 145, fourth line 140, cooling/heating source 105, and third line 135 ("cooling/heating source output fluid"). As a result, the proper blend of garment output fluid and cooling/heating source output fluid will be effected so as to achieve the desired fluid temperature at the garment's input port IP. Thus it will be seen that, as a result of this construction, the temperature of the working fluid being pulled from the garment G will remain substantially constant over the lifetime of cooling/heating source 105.

In essence, with the construction of FIG. 16, thermostatic mixing valve 110 acts to ensure a substantially constant temperature fluid is delivered to the input port IP of garment G; this construction can be advantageous, inasmuch as it maximizes the life of the cooling/heating source. With the construction of FIG. 17, thermostatic mixing valve 110 acts to ensure a substantially constant temperature fluid is passed out of the output port of garment G; this construction can be advantageous, inasmuch as it provides maximum responsiveness in the system to the varying workload of the user, by varying the temperature of the inlet fluid in proportion to that workload. In either case, however, the practical goal is the same, i.e., to maintain the user's body temperature at a substantially constant point.

Numerous advantages are achieved through the use of the present invention. Among these are:

(1) maximum efficiency—the use of the thermostatic mixing valve ensures that the working fluid is supplied to the garment at an appropriate temperature throughout the life of the cooling/heating source, thereby avoiding the excessive temperature differences typical of conventional systems (e.g., too cold at the start, too hot at the end, or vice versa) and their associated inefficient use of the specific and latent heat capacity of the cooling/heating source;

(2) maximum cooling/heating source life—since the working fluid is cooled/heated only as required, not constantly as in conventional systems, the life of the cooling/heating source is maximized;

(3) maximum wearer comfort—since the working fluid is supplied to the garment at a consistent temperature throughout the duty cycle, the "too cold/too hot" start associated with conventional systems is prevented, and the comfort of the user is maximized;

(4) universal cooling/heating source—the system is usable with any source of cooling or heating, i.e., thermal gel blocks, ice, water-activated chemical heaters, thermo-electric heat pumps, etc. can all be used with this system.

It should also be appreciated that numerous modifications may be made to the embodiments described above without departing from the scope of the present invention.

Thus, for example, in the preceding description it was indicated that pump 115 may be activated by the user through the use of an ordinary on-off switch. Alternatively, however, a thermostatic control switch 160 may be integrated into garment G to detect when the temperature of the working fluid in bladder B passes a pre-set threshold; when this occurs, the thermostatic control switch 160 will automatically activate pump 115 so as to move the working fluid through the garment and the cooling/heating source 105. Alternatively, thermostatic control switch 160 may be integrated into the garment's output port OP, or it may be integrated into the line connecting the garment's output port OP to system 100, or it may be located elsewhere within system 100. The use of a thermostatic control switch 160 can be convenient for the user and can help save energy by turning off pump 115 when it is not needed. However, with the present invention, thermostatic control switch 160 is not needed to conserve cooling/heating source 105, since thermostatic mixing valve 110 will direct fluid flow away from cooling/heating source 105 when it is not needed.

Still other changes will be obvious to persons skilled in the art in view of the present disclosure.

What is claimed is:

1. A fluid supply and conditioning system for use in conjunction with a garment having a fluid-impervious bladder with a first port and a second port, said system comprising:
    a cooling/heating source;
    a thermostatic mixing valve;
    a first line;
    a fourth line;
    a pump;
    said first line being connected to (i) the first port of the garment and (ii) said cooling/heating source and said thermostatic mixing valve;
    said fourth line being connected to (i) said cooling/heating source and (ii) said thermostatic mixing valve;
    said cooling/heating source being connected to said thermostatic mixing valve;
    said thermostatic mixing valve being connected to the second port of the garment; and
    said pump being interposed into one of said first line and said fourth line;
    whereby when a working fluid is circulated through the garment and said fluid supply and conditioning system, said thermostatic mixing valve ensures that fluid entering the bladder maintains a user's body temperature at a substantially constant point; and
    wherein said system further comprises a thermostatic control switch having a temperature sensor, and
    wherein said thermostatic control switch is adapted to activate said pump when its temperature sensor detects a temperature outside of a selected range.

2. A fluid supply and conditioning system according to claim 1 wherein said pump is adapted to move the working fluid out of the thermostatic mixing valve.

3. A fluid supply and conditioning system according to claim 1 wherein said pump is adapted to move the working fluid into the thermostatic mixing valve.

4. A fluid supply and conditioning system according to claim 1 wherein said pump comprises a diaphragm pump.

5. A fluid supply and conditioning system according to claim 1 wherein said pump comprises a piezo-electric pump.

6. A fluid supply and conditioning system according to claim 1 wherein said thermostatic mixing valve comprises a movable valve element.

7. A fluid supply and conditioning system according to claim 1 wherein said cooling/heating source comprises means chosen from the group consisting of an ice bath, a refrigerated supply source, a hot thermal gel bath, a cold thermal gel bath, an electrically-heated supply, and a thermo-electric heat pump.

8. A fluid supply and conditioning system according to claim 1 wherein said temperature sensor is disposed adjacent said bladder.

9. A personal cooling or warming system, said system comprising:
    a garment comprising:
        a carrier formed in the shape of the garment; and
        a bladder comprising at least two channel segments, wherein said channel segments have a substantially flat configuration, and wherein said bladder further comprises a first port and a second port; and
    a fluid supply and conditioning system for supplying temperature-conditioned fluid to said bladder, said fluid supply and conditioning system comprising:
        a cooling/heating source having a first port and a second port;
        a thermostatic mixing valve having a first port, a second port and a third port;
        a first line, and
        a pump;
        said first line being connected to (i) the first port of the garment and (ii) said first port of said cooling/heating source and said second port of said thermostatic mixing valve;
        said second port of said cooling/heating source being connected to said third port of said thermostatic mixing valve;
        said first port of said thermostatic mixing valve being connected to said second port of the garment; and
        said pump being interposed into one of said first line and said fourth line;
        whereby when a working fluid is circulated through the garment and said fluid supply and conditioning system, said thermostatic mixing valve will ensure that fluid entering the bladder will maintain the user's body temperature at a substantially constant point.

10. A garment according to claim 9 wherein a ribbon is disposed in said channels.

11. A garment according to claim 10 wherein said ribbon is relatively impervious to fluid flowing in said channels.

12. A garment according to claim 10 wherein said ribbon is relatively resistant to compressing.

13. A garment according to claim 10 wherein said ribbon is relatively impervious to fluid flowing in said channels and further wherein said ribbon is relatively resistant to compressing.

14. A garment according to claim 10 wherein said ribbon comprises a closed cell foam.

* * * * *